United States Patent [19]

Blake et al.

[11] 4,098,905

[45] Jul. 4, 1978

[54] TRIFLUOROETHANOL AS A MALE CONTRACEPTIVE

[75] Inventors: David Blake, Ellicott, Md.; Louis Ferstandig, Hackensack, N.J.

[73] Assignee: Halocarbon Products Corporation, Hackensack, N.J.

[21] Appl. No.: 715,074

[22] Filed: Aug. 17, 1976

[51] Int. Cl.² .......................................... A61K 31/045
[52] U.S. Cl. ................................................... 424/343
[58] Field of Search ......................................... 424/343

[56] References Cited

U.S. PATENT DOCUMENTS

| | | | |
|---|---|---|---|
| 3,193,573 | 7/1965 | Caldwell | 424/343 |
| 3,507,966 | 4/1970 | Arnold | 424/343 |
| 3,968,245 | 7/1976 | Higuchi | 424/343 |

*Primary Examiner*—Frederick E. Waddell
*Attorney, Agent, or Firm*—Burgess, Dinklage & Sprung

[57] ABSTRACT

The ability of a male to impregnate a female is reversibly effected by administering to the male, preferably daily in pill form, an effective amount of a trihalomethyl-containing lower alkanol, aldehyde, acid, amine, ether, or the like, or a derivative such as an amide or salt which liberates such compound in the body. The length of time needed for the male to regain his fertility depends upon the dosage of active material, preferably trifluoroethanol.

4 Claims, No Drawings

TRIFLUOROETHANOL AS A MALE CONTRACEPTIVE

The present invention relates to male contraceptives.

Various procedures are known for controlling conception and among the most reliable are surgical procedures such as tubal ligature for women and vasectomy for men. A problem with these techniques, however, is their permanence, i.e. irreversibility, although limited progress is being made in reversing vasectomies. For these reasons chemical means are most widely used and the most common chemicals are taken orally by women to prevent ovulation. This has gained wide acceptance but still has certain drawbacks. Insofar as the male is concerned, he cannot be certain the female has not failed to take the medication.

Even more important, the medication produces certain side effects, such as formation of blood clots in some women, so that at least for certain women it becomes inadvisable to utilize this technique for contraception. In such instances, it would be desirable if a chemical contraceptive procedure were available for the male mate of such susceptible female.

It is accordingly an object of the present invention to provide a composition for and method of effecting male contraception, which composition and method are simple, inexpensive, safe, reliable and temporary in character.

These and other objects and advantages are realized in accordance with the present invention pursuant to which it has been found that trihalomethyl-containing lower alkanols, aldehydes, acids, amines or derivatives thereof such as salts, ethers or amides which in the body hydrolyze to such compounds, have the capacity to effect contraception if taken by the male and such contraception is reversible if the compounds are taken in suitable dosages.

As employed hereinabove, the term "lower" has reference to up to about 5 carbon atoms although up to 4 and especially up to 3 is preferred. The amines, amides or ethers may contain further lower alkyl radicals. Preferably, the trihalomethyl radical includes fluorine as one of the halogen atoms, although chlorine, bromine and iodine are possibly present individually and/or in mixture with each other and/or fluorine. The preferred compound is trifluoroethanol, already available commercially in large quantities of high purity and relatively low cost.

The compounds can be administered in any conventional form such as by inhalation, injection, drinking of a solution or by orally taking pills. For ease of storage, certainty of dosage and certainty of administration, pills are preferred and the dosage is preferably adjusted so that the pill is taken once daily to establish a regimen which minimizes the likelihood of forgetting.

It is an advantage of the invention that, after an initial period of taking the active material, contraception is effected but, while reversible, there is a delay or recovery period so that failure to take the medication one day will not contravene the conceptive incapacity of the male even for that day.

The daily dosage may vary widely with safety but larger doses will tend to increase the length of the recovery period after which the male will again be able to impregnate the female. Doses of about 0.1 to 1000 mg/kg taken from 1 to 5 days apart are generally suitable. Taken in pill form on a daily basis this means preferably for males a dosage of about 0.1 to 200 mg.

The active materials are advantageously diluted with pharmacologically acceptable carriers and/or diluents. For administration as a solution the diluent is preferably water which may contain various flavoring agents, and the like. For administration by injection the diluent is preferably saline solution and injection may be intravenous, subcutaneous, or the like. For the preferred form as a pill the diluent or carrier may be lactose, glucose, starch, mannitol, magnesium stearate, microcrystalline cellulose, and the like. Other medicaments such as vitamins or the like may also be incorporated. The pills may be in the form of filled gelatin capsules, or can be compressed tablets or lozenges, in accordance with conventional pharmaceutical practice. Other adjuvants, such as lubricants or binding agents, for example, vegetable gums, or polyvinylpyrrolidone, may be incorporated into the dosage forms, if desired.

The safety and effectiveness of the active materials are shown in the following illustrative example.

EXAMPLE

One hundred forty sexually mature Sprague-Dawley strain rats (Charles River COBS), 100 males and 40 females, initially weighing between 257 and 425 grams, were used for this trial. The animals were divided by random selection from a pool of 110 males and 45 females into four groups of 25 males and 10 females each.

The animals in the treatment groups were exposed under dynamic conditions at a 100 liters/minute airflow in a 1000-liter glass and stainless steel Rochester-type inhalation chamber. Exposures were conducted 6 hours per day, 5 days a week, for four weeks. The air for the respective groups contained 0, 10 50 and 150 ppm of trifluoroethanol generated as a vapor by bubbling metered (low flow) nitrogen (98% pure) through a fritted glass tube submerged in trifluoroethanol in a 500 cc Erlenmeyer flask with a glass-wool filter plug in the effluent line prior to mixing with filtered air flowing into the chamber turret at 100 liters/minute, measured with a flowmeter. The groups are identified as 1, 2, 3 and 4, respectively.

After 20 exposure days and then starting 9 – 11 days later, 10 randomly selected males from each group were mated to a succession of five virgin sexually mature female rates (Sprague Dawley, Charles River COBS) each at weekly intervals. A total of 200 females were used as follows: Each male was placed with a single female for seven days (24 hours/day) and then shifted to another fresh female, etc. until five such pairings were completed.

Each female was sacrificed by chloroform overdose 19 days from the first day of pairing and was examined for evidence of fetal abnormalities, implantation and resorption sites, and corpora lutea.

After 10 exposure days, five males from each group were sacrificed by cervical dislocation and complete necropsies were performed. After 20 exposure days, 10 males and all surviving females from each group were similarly sacrificed and necropsied. The following organs were removed and fixed in 10% neutral buffered formalin:

| | | |
|---|---|---|
| brain | spleen | uterus |
| pituitary | adrenal | skin |
| eye | stomach | rib bone end |
| thyroid | pancreas | bone marrow |

-continued

| spinal cord | small intestine | nerve with adjacent |
| lung | large intestine | skeletal muscle |
| trachea | mesenteric lymph node | abnormal lesions |
| heart | urinary bladder | |
| liver | seminal vesicles | |
| kidney | gonads | |

The gonads from each animal were weighed. These weights were used to calculate gonad/body weight ratios.

Following 57 – 59 days of recovery the remaining males from each group were sacrificed with the testes removed and fixed.

Group mean body weights ± S.D. measured prior to exposure (Week 0) and weekly during the four weeks of exposure are presented in Table 1. Evaluation of these data did not indicate any effects relating to the exposure among the groups of males and females.

Table 1

Group mean body weights ±0 (S.D.) for male and female rats exposed to filtered air or to TFE vapor for four weeks.

MALES

| Group No. | 0 | 1 | 2 | 3 | 4 |
|---|---|---|---|---|---|
| 1 | 385 | 379 | 383 | 407 | 446 |
|  | (24) | (27) | (24) | (26) | (24) |
| 2 | 379 | 357 | 393 | 418 | 438 |
|  | (21) | (18) | (21) | (18) | (22) |
| 3 | 335 | 350 | 358 | 378 | 423 |
|  | (37) | (27) | (34) | (39) | (25) |
| 4 | 354 | 339 | 346 | 350 | 374 |
|  | (34) | (29) | (34) | (33) | (33) |

FEMALES

| Group No. | 0 | 1 | 2 | 3 | 4 |
|---|---|---|---|---|---|
| 1 | 282 | 277 | 287 | 297 | 292 |
|  | (13) | (14) | (16) | (15) | (24) |
| 2 | 286 | 276 | 300 | 312 | 297 |
|  | (14) | (14) | (15) | (18) | (18) |
| 3 | 280 | 281 | 295 | 294 | 292 |
|  | (20) | (21) | (19) | (19) | (40) |
| 4 | 279 | 277 | 287 | 290 | 283 |
|  | (7) | (10) | (11) | (10) | (11) |

With the exception of one male rat in Group 3, all animals exhibited normal appearance and behavior throughout the 4-week period. The exceptional rat appeared thin and exhibited a 60 gram weight loss after 2 weeks of exposure and a 3 gram weight loss after three weeks of exposure.

No deaths occurred among the groups of males and females.

Group mean data ± S.D. for terminal body weights, gonad weights, and gonad weight/body weight ratios for the five male rats from each group sacrificed after 10 exposure days (2 weeks) are presented in Table 2. Single classification analysis of various indicated that the mean testis weight and ratio for the Group 4 males was significantly lower than values obtained for the control males (Group 1).

Table 2

Group mean data ± (S.D.) for terminal body weights, organ weights, and organ/body weight ratios for male rats exposed to filtered air or to TFE vapor for two weeks.

| Group No. | Terminal Body Weight g | Testis Weight g | Testis Ratio % |
|---|---|---|---|
| 1 | 376 | 4.422 | 1.186 |
|  | (43) | (.140) | (.106) |
| 2 | 390 | 4.521 | 1.160 |
|  | (16) | (.255) | (.057) |
| 3 | 379 | 4.405 | 1.164 |
|  | (26) | (.245) | (.077) |
| 4 | 341* | 3.036* | .893* |
|  | (30) | (.314) | (.097) |

*Significantly lower than control.

Data for the 10 male and 10 female rats from each group sacrificed after 20 exposure days (4 weeks) are presented in Table 3. Single classification analysis of variance indicated that the terminal body weights and testis weights for the males in Groups 3 and 4 were significantly lower than values obtained for the control males. The testis/body weight ratio for the Group 4 males was significantly lower than the value obtained for the control males.

Analysis of the data for the female rats indicated that the ovary weight for the Group 2 females and the ovary weight/body weight ratios for the Group 3 females were significantly higher than values obtained for the control females.

Table 3

Group mean data ± (S.D.) for terminal body weights, organ weights, and organ/body weight ratios for male and female rats exposed to filtered air or to TFE vapor for four weeks.

MALES

| Group No. | Terminal Body Weight g | Testis Weight g | Testis Ratio % |
|---|---|---|---|
| 1 | 418 | 4.768 | 1.143 |
|  | (27) | (.512) | (.135) |
| 2 | 415 | 4.817 | 1.163 |
|  | (32) | (.412) | (.078) |
| 3 | 364* | 3.986* | 1.108 |
|  | (47) | (.397) | (.134) |
| 4 | 330* | 2.170* | .672* |
|  | (50) | (.176) | (.123) |

FEMALES

| group No. | Terminal Body Weight g | Ovary Weight g | Ovary Ratio % |
|---|---|---|---|
| 1 | 292 | .081 | .028 |
|  | (.018) | (.006) |  |
| 2 | 297 | .115** | .039** |
|  | (18) | (.017) | (.005) |
| 3 | 292 | .103 | .036** |
|  | (40) | (.015) | (.006) |
| 4 | 283 | .097 | .034 |
|  | (11) | (.019) | (.007) |

*Significantly lower than control.
**Significantly higher than control.

After 10 days exposure, five males from each group were sacrificed and the testes and epididymides were processed for histologic evaluation.

Selections from the Group 3 rats revealed occasional fusion bodies in the seminiferous tubules and epididymis apparently representing an early impairment of normal spermatogenesis.

Microscopic evaluation revealed hypospermatogenesis in the Group 4 rats. Hypospermatogenesis was characterized by decreased numbers of spermatozoa in the epididymis and varying numbers of seminiferous tubules in which incomplete spermatogenic activity was present characterized by the presence of spermatogonia and primary and occasional secondary spermatocytes with no evidence of spermatids. Multinucleated fusion bodies were also occasionally noted in seminiferous tubules and in the epididymis.

In the rats at 10 ppm spermatogenic activity was comparable to that noted in the control rats. After 20 exposure days, 10 males and the surviving females from each group were sacrificed and the gonads prepared for histologic evaluation.

Microscopic evaluation revealed marked hypospermatogenesis in the Group 4 male rats. Hypospermatogenesis was characterized by decreased numbers of spermatozoa in the epididymis and seminiferous tubules most of which were atrophic consisting of sertoli cells and spermatogonia with absence of spermatocytes or spermatids. Multinucleated fusion bodies were noted in seminiferous tubules and in the epididymis.

Sections of testes and epididymides from the Group 3 rats revealed occasional multinucleated fusion bodies in the seminiferous tubules and epididymis, apparently representing a minimal impairment of normal spermatogenesis. Essentially normal numbers of maturing spermatozoa were present in the epididymal ducts.

The rats in Group 2 had normal numbers of spermatozoa in the epididymal ducts and no evidence of impaired spermatogenesis in the seminiferous tubules.

Detailed histopathology as to tests and epididymides is presented in Tables 4 and 5.

Table 4

DETAILED HISTOPATHOLOGY INCIDENCE TABLE
10-DAY SACRIFICE

| | GROUP NUMBER 1 | | | | GROUP NUMBER 2 | | | | | |
|---|---|---|---|---|---|---|---|---|---|---|
| ORGANS | 3211 | 3212 | 3213 | 3224 | 3225 | 3236 | 3237 | 3238 | 3251 | 3252 |
| TESTES | X | X | X | X | X | X | X | X | X | X |
| Multinucleated Fusion Bodies | | | | | | | | | | |
| Hypospermatogenesis | | | | | | | | | | |
| EPIDIDYMIDES | X | X | X | X | | X | | X | X | X |
| Focal Nonsuppurative Epididymitis | | | | | | P | | P | | |
| Multinucleated Fusion Bodies | | | | | | | | | | |
| Decreased Numbers of Spermatozoa | | | | | | | | | | |

| | GROUP NUMBER 3 | | | | | GROUP NUMBER 4 | | | | |
|---|---|---|---|---|---|---|---|---|---|---|
| ORGANS | 3272 | 3273 | 3275 | 3286 | 3287 | 3311 | 3312 | 3313 | 3322 | 3323 |
| TESTES | | | | | | | | | | |
| Multinucleated Fusion Bodies | P | P | P | P | P | | P | P | P | P |
| Hypospermatogenesis | | | | | | P | P | P | P | P |
| EPIDIDYMIDES | | | | | | | | | | |
| Focal Nonsuppurative Epididymitis | | | | | | | | | | |
| Multinucleated Fusion Bodies | P | P | P | P | P | | P | P | P | P |
| Decreased Numbers of Spermatozoa | | | | | | P | P | P | P | |

P = Present
X = Not Remarkable

Table 5

DETAILED HISTOPATHOLOGY INCIDENCE TABLE
MALES
20-DAY SACRIFICE
GROUP NUMBER
GROUP 1 ANIMAL NUMBER

| ORGANS | 3214 | 3215 | 3216 | 3217 | 3218 | 3219 | 3220 | 3221 | 3222 | 3223 |
|---|---|---|---|---|---|---|---|---|---|---|
| TESTES | X | X | X | X | X | X | X | X | X | X |
| Multinucleated Fusion Bodies | | | | | | | | | | |
| Hypospermatogenesis | | | | | | | | | | |
| Dystrophic Mineralization | | | | | | | | | | |
| Seminiferous Tubules Contain Cell Debris | | | | | | | | | | |
| EPIDIDYMIDES | X | X | X | X | X | X | X | X | X | X |
| Focal Nonsuppurative Epididymitis | | | | | | | | | | |
| Multinucleated Fusion Bodies | | | | | | | | | | |
| Decreased Numbers of Spermatozoa | | | | | | | | | | |

MALES
20-DAY SACRIFICE
GROUP NUMBER
GROUP 2 ANIMAL NUMBER

| ORGANS | 3239 | 3240 | 3241 | 3242 | 3243 | 3244 | 3245 | 3246 | 3247 | 3248 |
|---|---|---|---|---|---|---|---|---|---|---|
| TESTES | X | X | X | X | | X | | X | X | X |
| Multinucleated Fusion Bodies | | | | | | | | | | |

Table 5-continued

DETAILED HISTOPATHOLOGY INCIDENCE TABLE

| | | | | | | | | | | |
|---|---|---|---|---|---|---|---|---|---|---|
| Hypospermatogenesis | | | | | | | | | | |
| Dystrophic Mineralization | | | | | | P | | P | | |
| Seminiferous Tubules Contain Cell Debris | | | | | | | | | | |
| EPIDIDYMIDES | X | X | X | X | X | X | X | X | X | X |
| Focal Nonsuppurative Epididymitis | | | | | | | | | | |
| Multinucleated Fusion Bodies | | | | | | | | | | |
| Decreased Numbers of Spermatozoa | | | | | | | | | | |

MALES 20-DAY SACRIFICE GROUP NUMBER
GROUP 3 ANIMAL NUMBER

| ORGANS | 3276 | 3277 | 3278 | 3279 | 3280 | 3281 | 3282 | 3283 | 3284 | 3285 |
|---|---|---|---|---|---|---|---|---|---|---|
| TESTES | P | P | P | P | P | P | P | P | P | P |
| Multinucleated Fusion Bodies | | | | | | | | | | |
| Hypospermatogenesis | | | | | P | | | | | |
| Dystrophic Mineralization | | | | P | P | | | P | | |
| Seminiferous Tubules Contain Cell Debris | | | | | | | | | | |
| EPIDIDYMIDES | | | | | | | P | | | P |
| Focal Nonsuppurative Epididymitis | P | P | P | P | P | P | P | P | P | P |
| Multinucleated Fusion Bodies | | | | | | P | | | | |
| Decreased Numbers of Spermatozoa | | | | | | | | | | |

MALES 20-DAY SACRIFICE GROUP NUMBER
GROUP 4 ANIMAL NUMBER

| ORGANS | 3291 | 3299 | 3314 | 3315 | 3316 | 3317 | 3318 | 3319 | 3320 | 3321 |
|---|---|---|---|---|---|---|---|---|---|---|
| TESTES | | | | | | | | | | |
| Multinucleated Fusion Bodies | | P | P | P | P | P | P | | | P |
| Hypospermatogenesis | P | P | P | P | P | P | P | P | P | P |
| Dystrophic Mineralization | | | | | | | | | P | |
| Seminiferous Tubules Contain Cell Debris | | | | | | | | | | |
| EPIDIDYMIDES | | | | | | | | | | |
| Focal Nonsuppurative EPIDIDYMITIS | | | | | | | | | | |
| Multinucleated Fusion Bodies | | | | | | | P | | | P |
| Decreased Number of Spermatozoa | P | P | P | P | P | P | P | P | P | P |

P = Present
X = Not Remarkable

The remaining organs listed above from each animal from the control group (Group 1) and from the group exposed to 148.74 ppm of TFE vapor (Group 4) sacrificed after 20 days of exposure were embedded in Paraplast ®, sectioned at five microns, slide mounted, and stained with hematoxylin and eosin. The slides were examined under a light microscope by a pathologist.

Microscopic evaluation conducted on the additional tissues from 10 male and 10 female rats of the control (Group 1) and high dose (Group 4) groups from the 20-day sacrifice failed to reveal histomorphologic alterations attributed to compound administration.

Sections of trachea from seven control and five treated rats revealed focal nonsuppurative tracheitis as a spontaneous disease lesion. Lung sections revealed early lesions of chronic murine pneumonia characterized by peribronchial and perivascular lymphoid hyperplasia along with focal accumulations of foamy macrophages, and an occasional focal area of pneumonitis in the control and treated rats with no evidence of increased severity due to compound administration.

Liver sections revealed microgranulomas in 17 of the control rats and 10 treated rats. In addition, minimal to slight nonsuppurative pericholangitis was present. Kidney sections revealed minimal to slight focal interstitial nephritis which was noted principally in the male rats. In the female rats, kidney sections revealed focal mineralization at the corticomedullary junction as an incidental finding unrelated to treatment. Occasional sections of large intestine revealed the presence of nematode parasite.

Focal nonsuppurative myocarditis was present in four control rats but was not observed in the treated animals. Sections of pancreas revealed occasional foci of nonsuppurative pancreatitis which in occasional animals was accompanied by degenerative changes in the acinar cells. These changes involved occasional lobules in the pancreas with the acinar cells in the remaining lobules being histologically normal. These alterations were considered incidental and unrelated to compound administration.

Detailed histopathology as to these organs is presented in Tables 6 and 7 which show there were no histomorphologic alterations attributed to compound administration in these additional tissues, i.e. the effect is limited to the testes.

Table 6
DETAILED HISTOPATHOLOGY INCIDENCE TABLE

MALES
20-DAY SACRIFICE
Group 1
ANIMAL NUMBER

| ORGANS | 3214 | 3215 | 3216 | 3217 | 3218 | 3219 | 3220 | 3221 | 3222 | 3223 |
|---|---|---|---|---|---|---|---|---|---|---|
| BRAIN | X | X | N | X | X | X | X | X | X | X |
| SPINAL CORD | X | X | N | N | X | X | X | X | N | X |
| PITUITARY | X | X | N | N | X | X | X | X | X | N |
| THYROID | X | X | X | X | X | X | X | X | X | X |
| ADRENAL | X | X | X | N | X | X | X | X | X | X |
| HEART | | X | N | N | X | X | X | | X | X |
| Focal Nonsuppurative Myocarditis | 1 | | | | | | | 2 | | |
| LUNG | | | | | | | | | | |
| Peribronchial Lymphoid Hyperplasia | 2 | 1 | 2 | 2 | 2 | 2 | 2 | 2 | 2 | 4 |
| Perivascular Lymphoid Hyperplasia | | 1 | 2 | 2 | 2 | | | | 2 | 2 |
| Foamy Macrophages | | P | P | | P | | | | | |
| Focal Pneumonitis | | | P | | | | | | | |
| SPLEEN | X | X | N | X | X | X | X | X | X | X |
| Focal Splenitis | | | | | | | | | | |
| LIVER | | | | | | | | | | |
| Microgranuloma | P | P | P | P | P | P | P | P | P | |
| Nonsuppurative Pericholangitis | 1 | | 1 | | | | | | 1 | 1 |
| KIDNEY | | | | | | | X | X | | X |
| Focal Interstitial Nephritis | 1 | 1 | 2 | 1 | 1 | 1 | | | 1 | |
| Focal Mineralization (corticomedullary junction) | | | | | | | | | | |
| STOMACH | X | X | N | X | X | X | X | X | X | X |
| SMALL INTESTINE | X | X | X | X | X | X | X | X | X | X |
| LARGE INTESTINE | X | X | X | N | X | X | X | X | X | |
| Nematode Parasite | | | | | | | | | | P |
| PANCREAS | X | X | X | X | X | | X | X | X | X |
| Focal Nonsuppurative Pancreatitis | | | | | | P | | | | |
| Degenerative Acinar Cells (lobular) | | | | | | | | | | |
| Ductal Cell Proliferation | | | | | | | | | | |
| Lobular Atrophy | | | | | | | | | | |
| SEMINAL VESICLE | X | X | N | N | X | X | X | X | X | X |
| MESENTERIC LYMPH NODE | X | X | X | N | X | X | X | X | X | X |
| URINARY BLADDER | X | X | N | N | X | X | X | X | X | X |
| NERVE | X | X | X | X | X | X | X | X | X | X |
| MUSCLE | X | X | X | X | X | X | X | X | X | X |
| EYE | X | X | X | X | X | X | X | X | X | X |
| COSTOCHONDRAL JUNCTION | X | X | N | X | X | X | X | X | X | X |
| BONE MARROW | X | X | X | X | X | X | X | X | N | X |
| SKIN | X | X | N | N | X | X | X | X | X | X |
| TRACHEA | | X | X | X | | X | X | | X | |
| Focal Nonsuppurative Tracheitis | 2 | | | | 2 | | | 2 | | 5 |

MALES
20-DAY SACRIFICE
GROUP 4
ANIMAL NUMBER

| ORGANS | 3291 | 3299 | 3314 | 3315 | 3316 | 3317 | 3318 | 3319 | 3320 | 3321 |
|---|---|---|---|---|---|---|---|---|---|---|
| BRAIN | X | X | X | X | X | X | X | X | X | X |
| SPINAL CORD | X | X | X | X | X | X | X | X | X | X |
| PITUITARY | X | X | X | X | X | X | X | X | X | X |
| THYROID | X | X | X | X | X | X | X | X | X | X |
| ADRENAL | X | X | X | X | X | X | X | X | X | X |
| HEART | X | X | X | X | X | X | X | X | X | X |
| Focal Nonsuppurative Myocarditis | | | | | | | | | | |
| LUNG | | | | | | | | | | |
| Peribronchial Lymphoid Hyperplasia | 3 | 1 | 2 | 2 | 1 | 2 | 2 | 1 | 3 | 1 |
| Perivascular Lymphoid Hyperplasia | 3 | 1 | 2 | | | 2 | 2 | | 3 | 1 |
| Foamy Macrophages | P | | | P | | | P | | P | |
| FOCAL Pneumonitis | P | | | | | | P | | P | |
| SPLEEN | X | X | X | X | | X | X | X | X | X |
| Focal Splenitis | | | | | P | | | | | |
| LIVER | X | | X | X | X | X | | X | X | X |
| Microgranuloma | | P | | | | | P | | | |
| Nonsuppurative Pericholangitis | | | | | | | 1 | | | |
| KIDNEY | X | X | X | X | | | | | | X |
| Focal Interstitial Nephritis | | | | | 1 | 1 | 1 | 2 | 1 | |
| Focal Mineralization (corticomedullary junction) | | | | | | | | | | |
| STOMACH | X | X | X | X | X | X | X | X | X | X |
| SMALL INTESTINE | X | X | X | X | X | X | X | X | X | X |
| LARGE INTESTINE | X | X | X | | X | N | X | X | X | X |
| Nematode Parasite | | | | P | | | | | | |
| PANCREAS | X | | | | | X | | X | X | X |
| Focal Nonsuppurative Pancreatitis | | P | | | P | | P | | | |
| Degenerative Acinar Cells | | | | | | | | | | |

Table 6-continued

| DETAILED HISTOPATHOLOGY INCIDENCE TABLE | | | | | | | | | | |
|---|---|---|---|---|---|---|---|---|---|---|
| (lobular) | | P | | P | | | | | | |
| Ductal Cell Proliferation | | | | | | | P | | | |
| Lobular Atrophy | | | | | | | | | | |
| SEMINAL VESICLE | X | X | X | X | X | X | X | X | X | X |
| MESENTERIC LYMPH NODE | N | X | X | X | X | X | X | X | X | X |
| URINARY BLADDER | X | X | X | X | X | X | X | X | X | X |
| NERVE | X | X | X | X | X | X | X | X | X | X |
| MUSCLE | X | X | X | X | X | X | X | X | X | X |
| EYE | X | X | X | X | X | X | X | X | X | X |
| COSTOCHONDRAL JUNCTION | X | X | X | X | N | X | X | X | X | X |
| BONE MARROW | X | X | X | X | N | X | X | X | X | X |
| SKIN | X | X | X | X | X | X | X | X | X | X |
| TRACHEA | | X | X | X | X | | X | X | X | X |
| Focal Nonsppurative | | | | | | | | | | |
| Tracheitis | 2 | | | | | 2 | | | | |

Table 7

| DETAILED HISTOPHATHOLOGY INCIDENCE TABLE | | | | | | | | | | |
|---|---|---|---|---|---|---|---|---|---|---|
| FEMALES | | | | | | | | | | |
| 20-DAY SACRIFICE | | | | | | | | | | |
| GROUP 1 | | | | | | | | | | |
| ANIMAL NUMBER | | | | | | | | | | |
| ORGANS | 3201 | 3202 | 3203 | 3204 | 3205 | 3206 | 3207 | 3208 | 3209 | 3210 |
| BRAIN | | | | | | | | | | |
| SPINAL CORD | | | | | | | N | | | |
| PITUITARY | | | | | | | | | | |
| THYROID | | | | | | | | | | |
| ADRENAL | | | | | | | | | | |
| HEART | | | | | | | | | | X |
| Focal Nonsuppurative Myocarditis | | | 1 | | | | | | 2 | |
| LUNG | | | | | | | | | | |
| Peribronchial Lymphoid Hyperplasia | 1 | 1 | 1 | 2 | 3 | 2 | 2 | 3 | 3 | 2 |
| Perivascular Lymphoid Hyperplasia | 1 | | | | | | | 1 | | |
| Foamy Macrophages | | | | | | | | | | |
| Focal Pneumonitis | | | | | | | | | | |
| SPLEEN | | | | | | | | | | |
| Focal Splenitis | | | | | | | | | | |
| LIVER | | | | | | | | | | |
| Microgranuloma | P | | P | P | P | | P | P | P | P |
| Nonsuppurative Pericholangitis | 1 | | 1 | 1 | | 1 | 1 | 1 | 2 | |
| KIDNEY | | | | | | | | | | |
| Focal Interstitial Nephritis | | | | | | | | | | |
| Focal Mineralization (corticomedullary junction) | P | P | P | P | | P | P | P | P | P |
| STOMACH | | | | | | | | | | |
| SMALL INTESTINE | | | | | | | | | | |
| LARGE INTESTINE | | | | | | | N | | | |
| Nematode Parasite | | | | P | | | | | | |
| PANCREAS | | | | | | | | | | |
| Focal Nonsuppurative Pancreatitis | | | P | | | | | | | |
| Degenerative Acinar Cells (lobular) | | | | | | | | | | |
| Ductal Cell Proliferation | | | P | | | | | | | |
| Lobular Atrophy | | | P | | | | | | | |
| UTERUS | | | P | | | | | | | |
| Hydrometra | | | | | | | | | | |
| MESENTERIC LYMPH NODE | | | | | | | | | | |
| URINARY BLADDER | | | | | | N | | | | |
| NERVE | | | | | | | | | | |
| MUSCLE | | | | | | | | | | |
| EYE | | | | | | | | | | |
| COSTOCHONDRAL JUNCTION | | | | N | | | | | | |
| BONE MARROW | | | | | | | | | | |
| SKIN | | | | N | | | | | | |
| TRACHEA | | | | | | | | | | |
| Focal Nonsuppurative Tracheitis | | 2 | | | | | | 2 | 2 | |

| | FEMALES | | | | | | | | | |
|---|---|---|---|---|---|---|---|---|---|---|
| | 20-DAY SACRIFICE | | | | | | | | | |
| | GROUP 4 | | | | | | | | | |
| | ANIMAL NUMBER | | | | | | | | | |
| ORGANS | 3334 | 3335 | 3336 | 3337 | 3338 | 3339 | 3340 | 3341 | 3342 | 3343 |
| BRAIN | | | | | | | | | | |
| SPINAL CORD | | | N | | | | | N | | |
| PITUITARY | | | | | | | | | | |
| THYROID | | | | | | | | | | |
| ADRENAL | | | | | | | | | | |
| HEART | | | | | | | | | | |
| Focal Nonsuppurative Myocarditis | | | | | | | | | | |

Table 7-continued

| DETAILED HISTOPHATHOLOGY INCIDENCE TABLE | | | | | | | | | | |
|---|---|---|---|---|---|---|---|---|---|---|
| LUNG | | | | | | | | | | |
| Peribronchial Lymphoid Hyperplasia | 2 | 2 | 1 | 2 | 1 | 2 | 2 | 1 | 2 | |
| Perivascular Lymphoid Hyperplasia | 2 | | 1 | | | 2 | | 1 | | 1 |
| Foamy Macrophages | P | | | | | | | | | |
| Focal Pneumonitis | | | | | P | P | | | | |
| SPLEEN | | | | | | | | | | |
| Focal Splenitis | | | | | | | | P | | |
| LIVER | | | | | | | | | | |
| Microgranuloma | P | P | P | | P | P | P | | P | P |
| Nonsuppurative Pericholangitis | 1 | 1 | 1 | 1 | 1 | | 1 | 1 | | |
| KIDNEY | | | | | | | | | | |
| Focal Interstitial Nephritis | | 1 | | | | 1 | 1 | | | |
| Focal Mineralization (corticomedullary junction) | P | P | P | P | P | P | P | P | P | P |
| STOMACH | | | | | | | | | | |
| SMALL INTESTINE | | | | | | | | | | |
| LARGE INTESTINE | | | | N | | | | | | |
| Nematode Parasite | | | | | | | | | | |
| PANCREAS | | | | | | | | | | |
| Focal Nonsuppurative Pancreatitis | P | | | | | P | | P | | |
| Degenerative Acinar Cells (lobular) | P | | | | | P | | P | | |
| Ductal Cell Proliferation | | | | | | | | | | |
| Lobular Atrophy | | | | | | | | | | |
| UTERUS | | | | | | | | | | |
| Hydrometra | | | | | | | | | | |
| MESENTERIC LYMPH NODE | | | | | | | | | | |
| URINARY BLADDER | | | | | | N | | | | |
| NERVE | | | | | | | | | | |
| MUSCLE | | | | | | | | | | |
| EYE | | | | | | | | | | |
| COSTOCHONDRAL JUNCTION | | | | | | | | | | |
| BONE MARROW | | | | | | | | | | |
| SKIN | | | | | | | | | | |
| TRACHEA | | | | | | | | | | |
| Focal Nonsuppurative Tracheitis | 2 | 2 | | | | | | 2 | | |

Sections of ovaries from all three treated groups revealed normal cyclic activity characterized by large corpora lutea and maturing follicles.

Detailed histopathology incidence tables are presented in Table 8.

Table 8

| DETAILED HISTOPATHOLOGY INCIDENCE TABLE | | | | | | | | | | |
|---|---|---|---|---|---|---|---|---|---|---|
| | FEMALES 20-DAY SACRIFICE GROUP NUMBER GROUP 1 ANIMAL NUMBER | | | | | | | | | |
| ORGANS | 3201 | 3202 | 3203 | 3204 | 3205 | 3206 | 3207 | 3208 | 3209 | 3210 |
| OVARY | | | | | | | | | | |
| Normal Cyclic Activity | P | P | P | P | P | P | P | P | P | P |
| Ovarian Cyst | | | | | | | | | | |
| | FEMALES 20-DAY SACRIFICE GROUP NUMBER GROUP 2 ANIMAL NUMBER | | | | | | | | | |
| ORGANS | 3249 | 3263 | 3264 | 3265 | 3266 | 3267 | 3268 | 3269 | 3270 | 3271 |
| OVARY | | | | | | | | | | |
| Normal Cyclic Activity | P | P | P | P | P | P | P | P | P | P |
| Ovarian Cyst | | | P | | | | | | | |
| | FEMALES 20-DAY SACRIFICE GROUP NUMBER GROUP 3 ANIMAL NUMBER | | | | | | | | | |
| ORGANS | 3301 | 3302 | 3303 | 3304 | 3305 | 3306 | 3307 | 3308 | 3309 | 3310 |
| OVARY | | | | | | | | | | |
| Normal Cyclic Activity | P | P | P | P | P | P | P | P | P | P |
| Ovarian Cyst | | | | | | | | | | |
| | FEMALES 20-DAY SACRIFICE GROUP NUMBER GROUP 4 ANIMAL NUMBER | | | | | | | | | |
| ORGANS | 3334 | 3335 | 3336 | 3337 | 3338 | 3339 | 3340 | 3341 | 3342 | 3343 |
| OVARY | | | | | | | | | | |
| Normal Cyclic Activity | P | P | P | P | P | P | P | P | P | P |

Table 8-continued

Ovarian Cyst

P = Present

Following 20 days exposure and then starting 9 – 11 days later, 10 males from each group were used in a reproduction study. After a 57 to 59-day recovery period, the males were killed and histologic sections of the testes and epididymides were evaluated. In the Group 4 rats a variable degree of residual response to trifluoroethanol exposure was evident. A slight to moderate bilateral hypospermatogenesis was present in seven rats, unilateral hypospermatogenesis in two rats, and in one rat both testes were histologically normal. In the testes from most rats, the seminiferous tubules were regaining normal spermatogenic activity with only scattered tubules revealing hypospermatogenesis. Also, increased numbers of immature precursor (spermatocytes) stages were present in the epididymal ducts.

Sections of the testes from the Group 2 and Group 3 rats were histologically comparable to the controls with normal spermatogenic activity.

Detailed histopathology incidence tables are presented in Table 9.

Table 9

| DETAILED HISTOPATHOLOGY INCIDENCE TABLE | | | | | | | | | | |
|---|---|---|---|---|---|---|---|---|---|---|
| MALES 57 → 59-DAY RECOVERY SACRIFICE | | | | | | | | | | |
| GROUP NUMBER | | | | | | | | | | |
| GROUP 1 | | | | | | | | | | |
| ANIMAL NUMBER | | | | | | | | | | |
| ORGANS | 3226 | 3227 | 3228 | 3229 | 3230 | 3231 | 3232 | 3233 | 3234 | 3235 |
| TESTES | | | | | | | | | | |
| Foci of Mononuclear Cells | X | X | X | X | X | X | X | X | X | X |
| Hypospermatogenesis, Bilateral | | | | P | | | | | | |
| Hypospermatogenesis, Unilateral | | | | | | | | | | |
| Dystrophic Mineralization | | | | | | | | | | |
| Multinucleated Fusion Bodies | | | | | | | | | | |
| DPIDIDYMIDES | | | | | | | | | | |
| Foci of Mononuclear Cells (Nonsuppurative Epididymitis) | X | X | X | | X | X | X | X | X | X |
| | | | | P | | | | | | |
| Hypospermatogenesis | | | | | | | | | | |
| Sperm Granuloma | | | | | | | | | | |
| Immature Forms (spermatocytes) | | | | | | | | | | |
| Multinucleated Fusion Bodes | | | | | | | | | | |

| | | | | | | | | | | |
|---|---|---|---|---|---|---|---|---|---|---|
| MALES 57 → 59-DAY RECOVERY SACRIFICE | | | | | | | | | | |
| GROUP NUMBER | | | | | | | | | | |
| GROUP 2 | | | | | | | | | | |
| ANIMAL NUMBER | | | | | | | | | | |
| ORGANS | 3253 | 3254 | 3255 | 3256 | 3257 | 3258 | 3259 | 3260 | 3261 | 3262 |
| TESTES | | | | | | | | | | |
| Foci of Mononuclear Cells | X | X | X | X | X | X | X | X | X | X |
| Hypospermatogenesis, Bilateral | | | | | | | | | | |
| Hypospermatogenesis, Unilateral | | | | | | | | | | |
| Dystrophic Mineralization | | | | | | | | | | |
| Multinucleated Fusion Bodies | | | | | | | | | | |
| EPIDIDYMIDES | | | | | | | | | | |
| Foci of Mononuclear Cells (Nonsuppurative Epididymitis) | X | X | X | X | X | X | X | | X | |
| Hypospermatogenesis | | | | | | | | P | | P |
| Sperm Granuloma | | | | | | | | | | |
| Immature Forms (spermatocytes) | | | | | | | | | | |
| Multinucleated Fusion Bodies | | | | | | | | | | |

| | | | | | | | | | | |
|---|---|---|---|---|---|---|---|---|---|---|
| MALES 57 → 59-DAY RECOVERY SACRIFICE | | | | | | | | | | |
| GROUP NUMBER | | | | | | | | | | |
| GROUP 3 | | | | | | | | | | |
| ANIMAL NUMBER | | | | | | | | | | |
| ORGANS | 3288 | 3289 | 3290 | 3297 | 3292 | 3293 | 3294 | 3295 | 3296 | 3298 |
| TESTES | X | X | X | X | X | X | X | X | X | X |
| Foci of Mononuclear Cells | | | | | | | | | | |
| Hypospermatogenesis, Bilateral | | | | | | | | | | |
| Hypospermatogenesis, Unilateral | | | | | | | | | | |
| Dystrophic Mineralization | | | | | | | | | | |
| Multinucleated Fusion Bodies | | | | | | | | | | |
| EPIDIDYMIDES | | | | | | | | | | |
| Foci of Mononuclear Cells (Nonsuppurative Epididymitis) | X | X | X | X | | X | X | X | X | X |
| Hypospermatogenesis | | | | | P | | | | | |
| Sperm Granuloma | | | | | | | | | | |
| Immature Forms (spermatocytes) | | | | | | | | | | |
| Multinucleated Fusion Bodies | | | | | | | | | | |

| | |
|---|---|
| MALES 57 → 59-DAY RECOVERY SACRIFICE | |
| GROUP NUMBER | |
| GROUP 4 | |
| ANIMAL NUMBER | |

Table 9-continued

| ORGANS | 3324 | 3325 | 3326 | 3327 | 3328 | 3329 | 3330 | 3331 | 3332 | 3333 |
|---|---|---|---|---|---|---|---|---|---|---|
| TESTES | X | | | | | | | | | |
| Foci of Mononuclear Cells | | | | | | | | | | |
| Hypospermatogenesis, Bilateral | | P | P | P | P | | P | P | P | |
| Hypospermatogenesis, Unilateral | | | | | | P | | | | P |
| Dystrophic Mineralization | | | | | | | P | P | | |
| Multinucleated Fusion Bodies | | | | | | P | P | | | |
| EPIDIDYMIDES | X | | | | | | | | | |
| Foci of Mononuclear Cells (Nonsuppurative Epididymitis) | | | | | | | | | | |
| Hypospermatogenesis | | P | P | P | P | P | | | P | P |
| Sperm Granuloma | | | | | | P | | | | |
| Immature Forms (spermatocytes) | | P | P | P | | | P | P | P | P |
| Multinucleated Fusion Bodies | | | | | | | | | | |

P = Present
X = Not Remarkable

The combined conception rates (Table 10 for the 5 weekly mating intervals were 94% (47/50), 96% (48/50), 72% (36/50), and 0% (0/50) for Groups 1, 2, 3, and 4, respectively. The conception rates for Group 2 were similar to those of the control group at all five mating intervals. The rates for Group 3 were lower than the control rates at Weeks 1 and 3, markedly lower than the control rate at Week 2, but similar to the control rates at Weeks 4 and 5. None of the females in Group 4 were pregnant at any of the five intervals.

Table 10

| | Conception rates (%) as evidenced by the presence of implantation sites. | | | |
|---|---|---|---|---|
| | Group No. | | | |
| Breeding Week | 1 | 2 | 3 | 4 |
| 1 | 90 | 80 | 60 | 0 |
| 2 | 90 | 100 | 30 | 0 |
| 3 | 100 | 100 | 80 | 0 |
| 4 | 100 | 100 | 90 | 0 |
| 5 | 90 | 100 | 100 | 0 |
| $\bar{X}$ | 94 | 96 | 72 | 0 |

Group mean values ± (S.D.) for the numbers of corpora lutea, implantation sites, resorption sites, and dead and live fetuses are presented in Table 11. Mean values for the indices of preimplantation loss, implantation efficiency, and postimplantation loss are presented in Tables 12, 13 and 14, respectively.

With the exception of a significantly lower preimplantation loss relative to the control group during Week 4 of the mating period, all values for Group 2 were comparable to the control group. (Pre-implantation loss = number of corpora lutea minus number of implantation sites.)

The mean numbers of corpora lutea found in the pregnant females in Group 3 were significantly lower than those of the control group at Weeks 1 and 3, but were comparable to the control group at Weeks 2, 4, and 5 of the mating period.

Comparison of mean numbers of corpora lutea among the pregnant control females and the non-pregnant females from all groups indicated no significant differences at any of the mating intervals, thus indicating that the females contributed nothing significant to the differences between groups, as far as conception rates are concerned.

The mean numbers of implantation sites for the Group 3 females were significantly lower than the control means at Weeks 1 and 3 and were quantitatively, although not significantly, lower at Week 2. Preimplantation loss, presented in Table 12, for this group was significantly higher at Weeks 2 and 3 than the values obtained for the control group. Corresponding decreases in implantation efficiency (number of implantation sites/number of corpora lutea X 100) were indicated for Group 3 at Weeks 2 and 3 (Table 13).

The mean numbers of live fetuses in Group 3 were significantly lower than the control means at Weeks 1 and 3 and were quantitatively, although not significantly, lower at Week 2. Although these differences were not correspondingly reflected in the mean numbers of resorption sites and dead fetuses, comparisons of the postimplantation losses (number of resorptions + dead fetuses/number of implantation sites) between these two groups, which represents the relative number of fetal deaths, revealed a marked increase in the number of resorptions in Group 3 at Week 1 and increases of less significance at Weeks 2 and 3 as noted in Table 14.

The numbers of females in Groups 2 and 3 with one or more, or two or more dead implantations were comparable to the numbers in the control group at all five mating intervals.

In summary, the exposure of the rats to 149 ppm trifluoroethanol vapor for 10 and 20 days resulted in marked hypospermatogenesis and a concomitant absence of conception throughout a 5-week serial mating study, initiated 9 days after exposure. However, the testes from the males sacrificed following a 57-day recovery period revealed regeneration with normal spermatogenesis in many seminiferous tubules. The exposure of rats to 49 ppm of trifluoroethanol vapor for 20 days resulted in minimal hypospermatogenesis and increased preimplantation losses during the second and third weeks of the serial mating study. Normal spermatogenesis was present in the males from this group sacrificed after a 58-day recovery period.

Other organs were substantially unaffected.

Table 11

| | | Group mean ovarian and uterine data ± (S.D.) for pregnant females. | | | |
|---|---|---|---|---|---|
| Observation | Breeding Week | Group No. | | | |
| | | 1 | 2 | 3 | 4 |
| Ovarian Corpora Lutea | 1 | 15.8 (3.0) | 15.0 (2.1) | 11.7* (2.3) | — |
| | 2 | 15.3 (3.2) | 16.2 (1.5) | 17.0 (2.0) | — |
| | 3 | 15.1 (2.4) | 13.9 (1.2) | 10.4* (5.4) | — |
| | 4 | 15.8 (2.5) | 14.9 (1.8) | 17.4 (1.5) | — |
| | 5 | 15.0 (2.1) | 15.5 (2.8) | 15.0 (2.1) | — |
| Uterine Implantation Sites | 1 | 10.7 (1.7) | 11.5 (1.9) | 7.2* (3.3) | — |
| | 2 | 12.4 (4.2) | 12.9 (1.2) | 8.3 (4.2) | — |
| | 3 | 12.7 (2.3) | 12.9 (1.0) | 5.9* (5.4) | — |
| | 4 | 11.4 (4.4) | 13.5 (1.6) | 12.1 (3.8) | — |

Table 11-continued

Group mean ovarian and uterine data ± (S.D.) for pregnant females.

| Observation | Breeding Week | Group No. 1 | 2 | 3 | 4 |
|---|---|---|---|---|---|
| | 5 | 12.7 | 13.2 | 13.1 | — |
| | | (2.8) | (2.1) | (1.8) | — |
| | 1 | 0.4 | 0.6 | 1.2 | — |
| | | (0.5) | (0.9) | (2.0) | — |
| | 2 | 0.7 | 0.8 | 1.0 | — |
| | | (0.7) | (0.8) | (1.0) | — |
| Resorption | 3 | 0.2 | 0.6 | 0.3 | — |
| Sites | | (0.4) | (0.7) | (0.5) | — |
| | 4 | 1.2 | 0.6 | 1.2 | — |
| | | (0.9) | (0.7) | (1.4) | — |
| | 5 | 1.3 | 0.4 | 0.6 | — |
| | | (1.2) | (0.7) | (1.0) | — |
| | 1 | 10.2 | 10.9 | 6.0* | — |
| | | (1.4) | (1.5) | (2.8) | — |
| | 2 | 11.7 | 12.0 | 7.3 | — |
| | | (3.9) | (0.9) | (4.0) | — |
| Live Fetuses | 3 | 12.5 | 12.3 | 5.5* | — |
| | | (2.3) | (1.3) | (5.4) | — |
| | 4 | 10.2 | 12.9 | 10.9 | — |
| | | (4.0) | (1.6) | (3.2) | — |
| | 5 | 11.3 | 12.8 | 12.5 | — |
| | | (3.5) | (2.4) | (2.0) | — |
| | 1 | 0.0 | 0.0 | 0.0 | — |
| | | (0.0) | (0.0) | (0.0) | — |
| | 2 | 0.1 | 0.1 | 0.0 | — |
| | | (0.3) | (0.3) | (0.0) | — |
| Dead Fetuses | 3 | 0.0 | 0.0 | 0.1 | — |
| | | (0.0) | (0.0) | (0.4) | — |
| | 4 | 0.0 | 0.0 | 0.0* | — |
| | | (0.0) | (0.0) | (0.0) | — |
| | 5 | 0.0 | 0.0 | 0.0 | — |
| | | (0.0) | (0.0) | (0.0) | — |

*Significantly lower than control at $p \leq 0.05$.

Table 12

Preimplantation loss (number of corpora lutea - number of implantations) for pregnant females.

| Breeding Week | Group No. 1 | 2 | 3 | 4 |
|---|---|---|---|---|
| 1 | 5.1 | 3.5 | 4.5 | — |
| | (3.7) | (1.8) | (1.6) | — |
| 2 | 2.9 | 3.3 | 8.7** | — |
| | (1.9) | (2.3) | (3.1) | — |
| 3 | 2.4 | 1.0 | 4.5** | — |
| | (1.8) | (1.3) | (2.4) | — |
| 4 | 4.4 | 1.4* | 5.3 | — |
| | (3.2) | (1.0) | (3.0) | — |
| 5 | 2.3 | 2.3 | 1.9 | — |
| | (3.5) | (1.8) | (1.4) | — |
| | (3.5) | (1.8) | (1.4) | — |

*Significantly lower than control at $p \leq 0.05$.
**Significantly higher than control at $p \leq 0.05$.

Table 13

Implantation efficiency [% (Number of implantations/number of corpora lutea × 100)] for pregnant females.

| Breeding Week | Group No. 1 | 2 | 3 | 4 |
|---|---|---|---|---|
| 1 | 67.6 | 76.7 | 61.4 | 0 |
| 2 | 81.2 | 79.6 | 49.0 | 0 |
| 3 | 84.1 | 92.8 | 56.6 | 0 |
| 4 | 72.2 | 90.6 | 69.4 | 0 |
| 5 | 84.4 | 85.2 | 87.3 | 0 |
| X | 77.9 | 85.0 | 64.7 | 0 |

Table 14

Postimplantation loss indices [% (number of dead implantations/number of implantations × 100)] for pregnant females.

| Breeding Week | Group No. 1 | 2 | 3 | 4 |
|---|---|---|---|---|
| 1 | 4.2 | 5.4 | 16.3 | 0 |
| 2 | 6.3 | 7.0 | 12.0 | 0 |
| 3 | 1.6 | 4.7 | 6.4 | 0 |
| 4 | 10.5 | 4.4 | 10.1 | 0 |
| 5 | 10.5 | 3.0 | 4.6 | 0 |
| X | 6.6 | 4.9 | 9.9 | 0 |

It will be appreciated that the instant specification and examples are set forth by way of illustration and not limitation, and that various modifications and changes may be made without departing from the spirit and scope of the present invention.

What is claimed is:

1. A method of preventing a male from impregnating a female comprising administering internally to said male a contraceptively effective amount of trifluoroethanol.

2. The method according to claim 1, wherein the trifluoroethanol is administered daily in the form of a pill or capsule and at a dosage of about 0.1 to 1000 mg.

3. A male contraceptive pill or capsule suitable for taking orally and consisting essentially of a male contraceptively effective amount of a trifluoroethanol, and a pharmacologically acceptable diluent.

4. A pill or capsule according to claim 3, containing about 0.1 to 1000 mg of the active compound.